United States Patent
Lee

(10) Patent No.: US 11,291,742 B1
(45) Date of Patent: Apr. 5, 2022

(54) AIR STERTILIZATION LAMP DEVICE

(71) Applicant: S.M.Doctor Co.,Ltd, Gyeonggi-do (KR)

(72) Inventor: Changho Lee, Gyeonggi-do (KR)

(73) Assignee: S.M.DOCTOR CO., LTD, Gyeonggi-Do (KR)

( * ) Notice: Subject to any disclaimer, the term of this patent is extended or adjusted under 35 U.S.C. 154(b) by 0 days.

(21) Appl. No.: 17/148,969

(22) Filed: Jan. 14, 2021

(30) Foreign Application Priority Data

Sep. 22, 2020  (KR) .......................... 10-2020-0122158

(51) Int. Cl.
*A61L 9/18* (2006.01)

(52) U.S. Cl.
CPC ............. *A61L 9/18* (2013.01); *A61L 2209/12* (2013.01)

(58) Field of Classification Search
CPC ...... A61L 9/18; A61L 9/205; A61L 2209/111; A61L 2209/12
See application file for complete search history.

(56) References Cited

U.S. PATENT DOCUMENTS

| | | | | |
|---|---|---|---|---|
| 10,328,174 | B2* | 6/2019 | Jaworski | .................. A61L 2/202 |
| 10,584,886 | B2* | 3/2020 | Goswami | .................. A61L 9/22 |
| 2015/0147240 | A1* | 5/2015 | Chang | ..................... H01L 33/44 422/186 |
| 2017/0082305 | A1* | 3/2017 | Law | .................... B01D 46/0036 |
| 2020/0139000 | A1 | 5/2020 | Maa et al. | |

FOREIGN PATENT DOCUMENTS

| | | |
|---|---|---|
| JP | 2010-017691 A | 1/2010 |
| KR | 20-0348511 Y1 | 4/2004 |
| KR | 10-2010-0029668 A | 3/2010 |
| KR | 10-2011-0013921 A | 2/2011 |
| KR | 10-2015-0089704 A | 8/2015 |
| KR | 10-2016-0065389 A | 6/2016 |

(Continued)

OTHER PUBLICATIONS

Zhang and Liu. "Visible-light-induced degradation of formaldehyde over titania photocatalyst co-doped with nitrogen and nickel." Applied Surface Science 254 (2008) 4780-4785. (Year: 2008).*

(Continued)

*Primary Examiner* — Timothy C Cleveland
(74) *Attorney, Agent, or Firm* — The PL Law Group, PLLC

(57) ABSTRACT

An air sterilization lamp device according to an embodiment of the present disclosure includes a body in which an intake fan is installed and which suctions outside air through an intake hole provided in the outer surface thereof and is coated with a coating solution containing a photocatalytic material, a lamp which is connected to and installed in the body and through which the outside air suctioned into the body is introduced, and a light emitting source installed inside the lamp and configured to emit light by power supplied from the body. According to the present disclosure, an air sterilization lamp device that can purify indoor air through a function of removing to generated fine dust and performing sterilization treatment as the lamp coated with the coating solution containing the photocatalytic material is irradiated with light, and can simultaneously function as lighting is provided.

7 Claims, 4 Drawing Sheets

(56) References Cited

FOREIGN PATENT DOCUMENTS

KR     10-2042655  B1   11/2019
WO     02/102497   A1   12/2002

OTHER PUBLICATIONS

Office action dated Dec. 7, 2020 from Korean Patent Office in a counterpart Korean Patent Application No. 10-2020-0122158 (all the cited references are listed in this IDS.) (English translation is also submitted herewith.).
Notice of Allowance dated Jul. 23, 2021 from Korean Patent Office in a counterpart Korean Patent Application No. 10-2020-0122158 (all the cited references are listed in this IDS.) (English translation is also submitted herewith.).

* cited by examiner

AIR STERILIZATION LAMP DEVICE

CROSS-REFERENCE TO RELATED APPLICATION

This application claims the benefit under 35 USC § 119(a) of Korean Patent Application No. 10-2020-0122158 filed on Sep. 22, 2020, in the Korean Intellectual Property Office, the entire disclosure of which is incorporated herein by reference for all purposes.

BACKGROUND

1. Field of the Invention

The present disclosure relates to an air sterilization lamp device, and more particularly, to an air sterilization lamp device by which indoor air is purifiable through a function of removing generated fine dust and performing sterilization treatment as a lamp coated with a coating solution containing a photocatalytic material is irradiated with light and, at the same time, which is functional as a lighting device.

2. Discussion of Related Art

In recent years, the use of air purifiers in homes, offices, hospitals, and the like is rapidly increasing due to an increase in air pollution and fine dust. However, air purifiers according to the related art have a technical limitation in that the air purifier performs only a function of purifying air through a built-in physical and chemical filter and cannot provide additional functions such as indoor lighting and air sterilization.

Meanwhile, most lighting devices used for indoor lighting effects have technical limitations in that the lighting devices perform only functions of indoor lighting and interior decoration but cannot provide additional functions such as air purification and sterilization treatment.

SUMMARY

An aspect of the present disclosure is to provide an air sterilization lamp device capable of purifying indoor air through a function of removing generated fine dust and performing sterilization treatment as a lamp coated with a coating solution containing a photocatalytic material is irradiated with light and, at the same time, serving as a lighting device.

In order to achieve the aspect, an air sterilization lamp device according to the present disclosure includes: a body in which an intake fan is installed and which suctions outside air through an intake hole provided in an outer surface of the body; a lamp which is connected to and installed in the body and through which the outside air suctioned into the body is introduced; and a light emitting source installed inside the lamp and configured to emit light by power supplied from the body.

The air sterilization lamp device may further include a filter installed between the body and the lamp and coated with a photocatalytic material.

The air sterilization lamp device may further include an input part through which an operation command of a user for the air sterilization lamp device is input.

A sensor configured to measure the concentration of fine dust in the outside air introduced through the intake hole and configured to measure the concentration of volatile organic compounds contained in the outside air may be installed in the body.

The surface of the lamp may be heat-treated after being coated with a solution containing a photocatalytic material, and the surface of the lamp may be irradiated with light having a wavelength of 580 nm to 640 nm through the coating treatment.

The fine dust and the volatile organic compounds contained in the outside air introduced through the intake hole inside the lamp may be removed by the light with which the surface of the lamp is irradiated.

The photocatalytic material may contain titanium dioxide.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION

Figure 1:
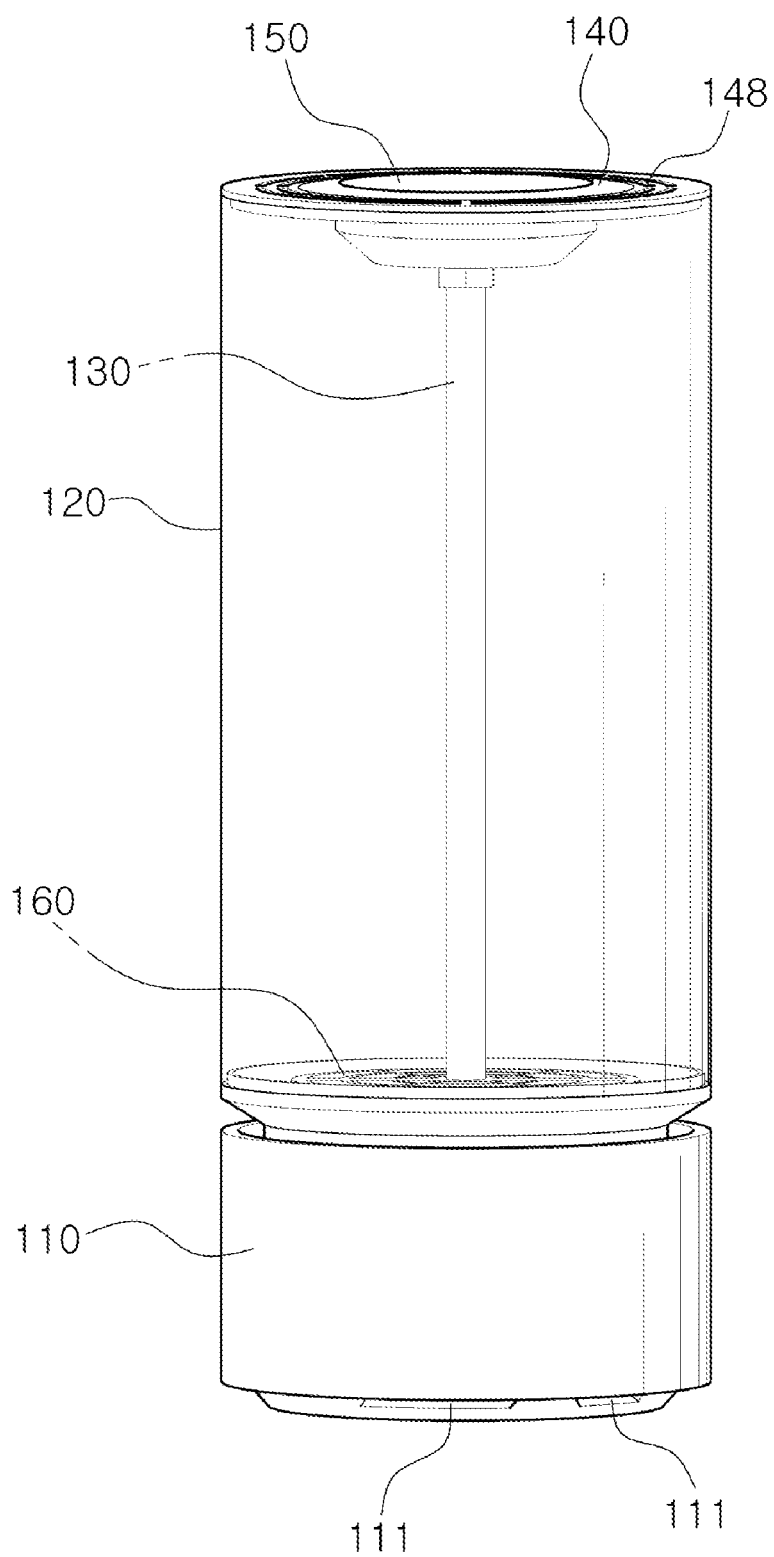
FIG. 1 is a perspective view of an air sterilization lamp device according to an embodiment of the present disclosure.

Hereinafter, the present disclosure will be in more detail with reference to the accompanying drawings. It should be noted that the same components in the drawings are indicated by the same reference numerals wherever possible. Further, the detailed description of well-known functions and configurations, which may make the subject matter of the present disclosure unclear, will be omitted.

Figure 2:
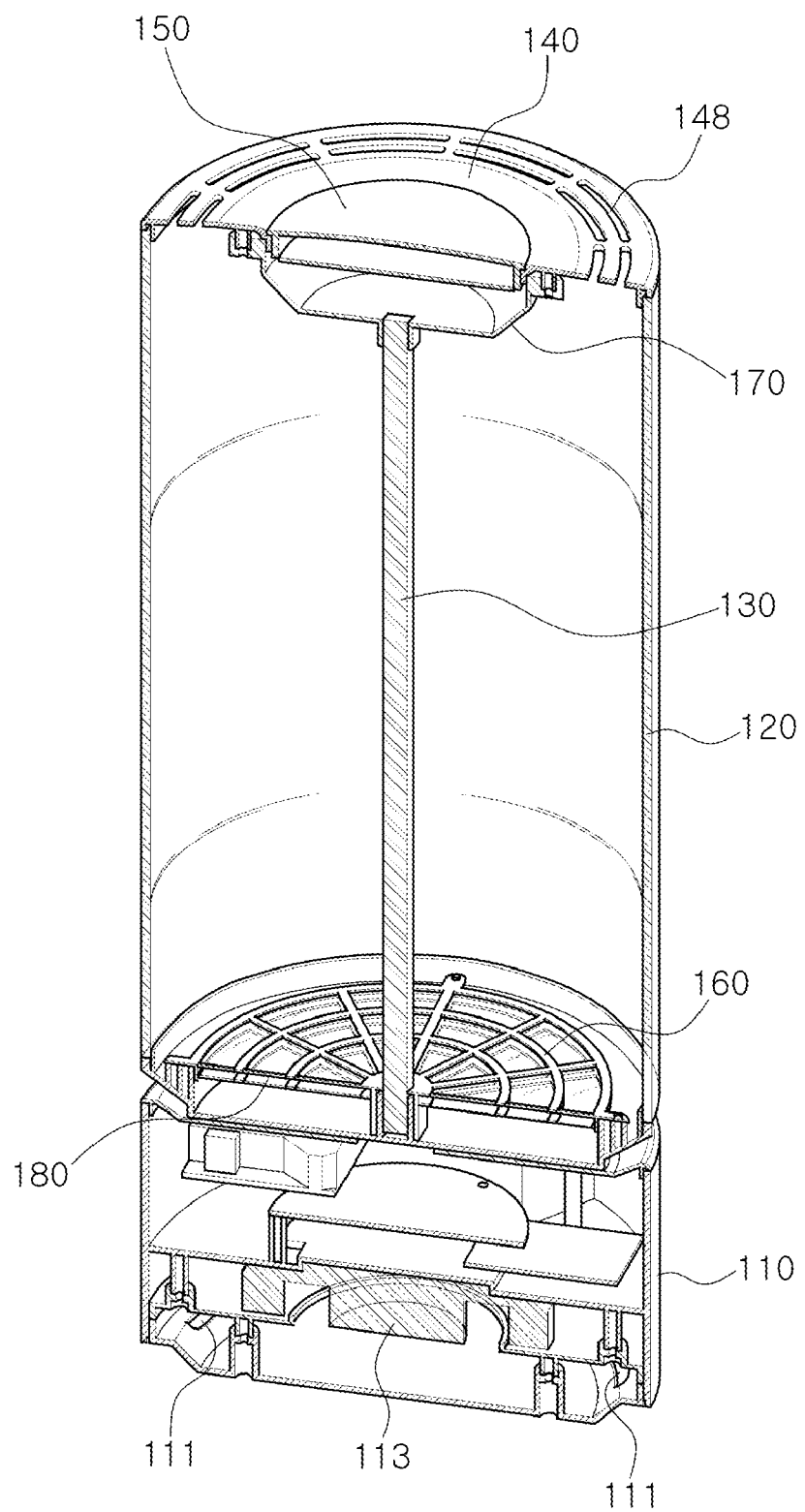
FIG. 2 is a vertical sectional view illustrating an internal structure of the air sterilization lamp device according to the embodiment of the present disclosure.

FIG. 1 is a perspective view of an air sterilization lamp device according to an embodiment of the present disclosure, and FIG. 2 is a vertical sectional view illustrating an internal structure of the air sterilization lamp device according to the embodiment of the present disclosure.

Referring to FIGS. 1 and 2, the air sterilization lamp device according to the embodiment of the present disclosure includes a body 110, a lamp 120, a light emitting source 130, an input part 140, a display part 150, and a filter 160.

An intake fan 113 is installed inside the body 110, and as the intake fan 113 is driven, outside air is introduced into the body 110 through an intake hole 111 provided in the outer surface (for example, the bottom surface) of the body 110.

Further, in the implementation of the present disclosure, it is preferable that a sensor configured to measure a concentration of fine dust in the outside air introduced through the intake hole 111 and a sensor configured to measure the concentration of organic compounds contained in the outside air are installed in the body 110.

The lamp 120, which is a transparent or translucent cylindrical structure in which the light emitting source 130 is installed, is connected to and installed on an upper portion of the body 110, and the outside air suctioned into the body 110 through the intake hole 111 is primarily purified while passing through the filter 160 installed at a connection portion between the body 110 and the lamp 120, and is then introduced into the lamp 120.

Meanwhile, in the implementation of the present disclosure, the lamp 120 may be a cylindrical structure having various shapes such as a cylindrical shape and a semi-cylindrical shape.

As the light emitting source 130, such as a light emitting diode (LED), which emits light by power supplied from the body 110, is installed in the inner center of the lamp 120 in a lengthwise direction of the lamp 120, the lamp 120 functions as a lamp housing that radiates the light irradiated from the internal light emitting source 130 to the outside.

Meanwhile, as illustrated in FIG. 2, the light emitting source 130 manufactured in a bar shape has one end fixedly installed in an upper housing 170 in which the input part 140 and the display part 150 are installed and has the other end fixedly installed in a lower housing 180 in which the filter 160 is installed.

It is preferable that the lamp 120 is made of a polycarbonate material, and it is preferable that the inner surface and the outer surface of the lamp 120 are coated with a coating solution, which is a solution containing a photocatalytic material, and are then heat-treated.

In detail, the photocatalytic material contained in the coating solution according to the embodiment of the present disclosure may be N- and Ni-codoped $TiO_2$ (NNT) prepared through a sol-gel reaction as a photosensitive photocatalytic material for visible light.

In detail, in order to prepare an NNT photocatalyst, the present inventor allowed a mixed solution of a 0.1M titanium tetra isopropoxide solution (St. Louis, Mo., 99%), 1.2M diethanolamine (Sigma, St. Louis, Mo., 99%), and 800 mL of 2-propanol (Duksan, Ansan, 98.5%) to react while stirring the mixed solution at room temperature for about 5 hours to obtain a $TiO_2$ sol, and injected nickel(II) chloride hexahydrate ($NiCl_2.6H_2O$; Wako, Osaka, Japan, 98%) into the sol.

Meanwhile, by adjusting the amount of injected nickel(II) chloride hexahydrate ($NiCl_2.6H_2O$; Wako, Osaka, Japan, 98%), the amount of Ni was made to be 2% based on the mass of $TiO_2$ in the solution, and the mixture produced in this way was stirred at room temperature for about 5 hours.

For N-doping, 0.05M ammonium carbonate (($NH_4)_2CO_3$, Samcheon, Seoul, Korea, 30.0%) was injected and stirred for 12 hours to obtain an NNT sol.

In detail, $TiO_2$ as a photocatalyst was codoped with nitrogen (N) ions and metal (Ni) ions, and thus the physicochemical properties and optical properties of $TiO_2$ can be improved. In detail, chemically stable $TiO_2$ was codoped with nitrogen (N) ions and metal (Ni) ions, and thus a band gap can be reduced.

Further, NNT nanocrystals prepared in this way have a property of absorbing ultraviolet light and visible light having wavelengths of up to about 600 nm and have excellent visible light sensitivity, and thus energy consumption of a light source in a photocatalytic reaction can be reduced.

Figure 3:
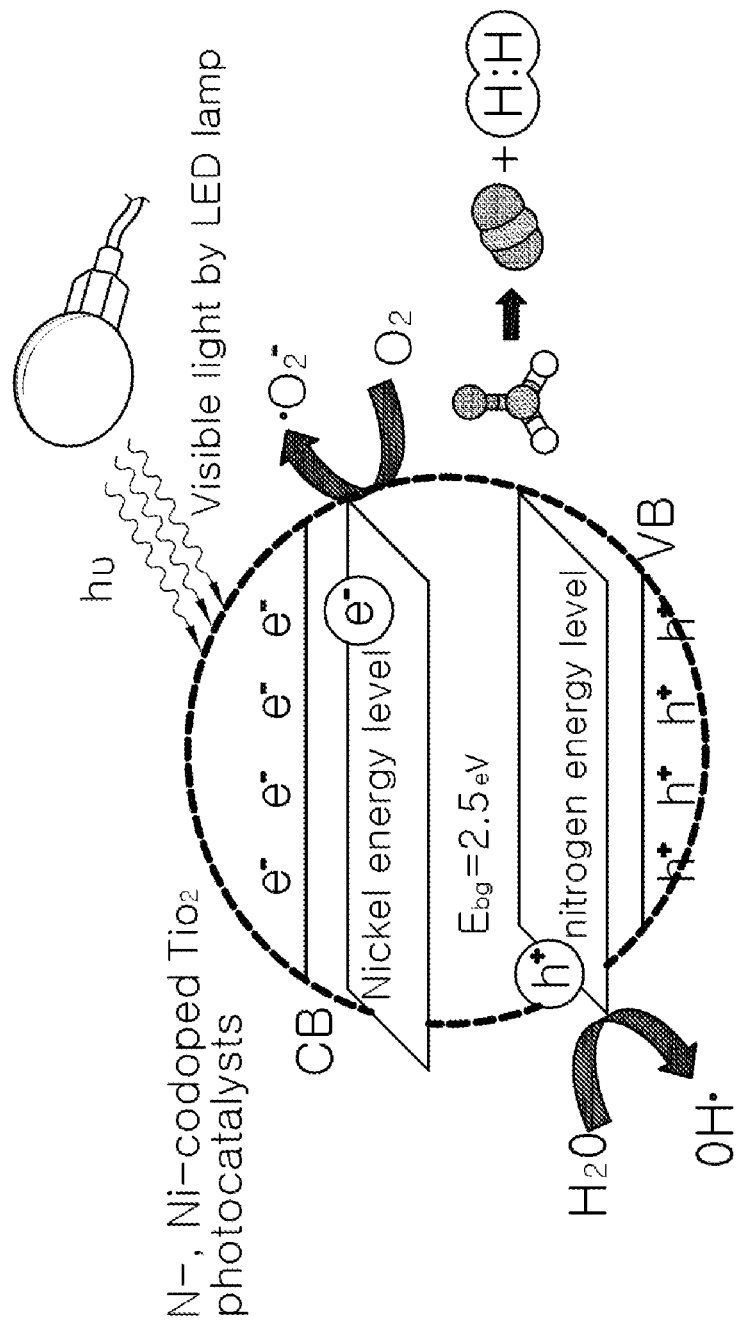
FIG. 3 is a view for describing a phenomenon occurring when a photocatalytic material is irradiated with visible light according to the embodiment of the present disclosure.

Meanwhile, in relation to this, FIG. 3 illustrates a phenomenon that occurs when the photocatalytic material according to the embodiment of the present disclosure is irradiated with visible light.

It is preferable that a dip coating method is used when the surface of the lamp 120 made of polycarbonate is coated with the NNT. In detail, dip coating may be performed by immersing the lamp 120 in the NNT, which is a photocatalyst in a sol state, and then slowly pulling the lamp 120 upward so that an NNT coating film is formed on the inner and outer surfaces of the lamp 120.

It is preferable that after such coating treatment, the lamp 120 is dried at room temperature for about 12 hours, and the coated thin film is then dried at 130° C. in a dryer such as an oven.

Meanwhile, since the glass transition temperature of the polycarbonate is 147° C., and thus the heat resistance thereof is not good, it is preferable that the drying treatment is performed at a temperature lower than the glass transition temperature (147° C.).

As described above, as the surface of the lamp 120 made of polycarbonate is coated with the NNT, degradation of the polycarbonate due to ultraviolet absorption can be suppressed, contaminants on the surface of the lamp 120 can be photodecomposed, and indoor air can be purified and fine dust can be removed through a photocatalytic reaction of the thin film coated NNT.

Meanwhile, the present inventor confirmed that in a state in which power is supplied to the light emitting source 130 and the lamp 120 is irradiated with light, *Escherichia coli*, *Staphylococcus aureus*, and *Pseudomonas aeruginosa* are sterilized on the inner and outer surfaces of the lamp 120 coated as described above, and confirmed that formaldehyde (HCHO) is decomposed in the inner space and the outer space of the lamp 120.

Experimental Example

In detail, the present inventor tested formaldehyde removal performance in a state in which the lamp 120 coated with the NNT was emitting light as described above.

In detail, the present inventor produced a gas-phase test box having a width of 35 cm, a length of 50 cm, and a height of 30 cm, and the initial concentration of formaldehyde (Duksan, Ansan, Korea, 40%) measured using gas chromatography equipment in a state in which the formaldehyde was injected into the gas-phase test box was 150 ppm.

Thereafter, as the lamp 120 coated as described above was installed inside the corresponding gas-phase test box and power was supplied to the lamp 120, a light emitting state was maintained.

The present inventor confirmed that the concentration of formaldehyde decreased by about 45% after 1 hour of light emission of the lamp 120, and confirmed that the concentration of formaldehyde decreased by about 90% after 2 hours.

In addition, according to the present disclosure, as the coating solution having the above-described component is applied to the surface of the lamp 120 made of polycarbonate, conventional wavelength attenuation of light generated while light is radiated to the outside through the lamp 120 does not occur, and thus wavelength characteristics of the lamp 120 can be improved.

In detail, as a result of an experiment conducted in a state in which the coating solution having the above-described component was applied to the surface of the lamp 120 made of polycarbonate, the present inventor confirmed that light, which was irradiated from a light source such as an LED installed inside the lamp 120 and had a wavelength in the range of 580 nm to 640 nm, which is a visible light region, was measured to have the same wavelength range (580 nm to 640 nm) even when the light was measured outside the surface of the lamp 120.

In more detail, as a result of an experiment conducted in a state in which the coating solution having the above-described component was applied to the surface of the lamp 120 made of polycarbonate and the light source such as the LED that irradiates light having a dominant wavelength of 601 nm in the wavelength range was installed in the lamp, the present inventor confirmed that the light was measured to have the same wavelength (601 nm) even when the light was measured outside the surface of the lamp 120.

Further, the coating solution according to another embodiment of the present disclosure may include 4 to 15 parts by weight of the NNT, 30 to 40 parts by weight of an alkoxide, and 45 to 55 parts by weight of ethanol.

The NNT and the alkoxide, which are photocatalytic materials contained in the coating solution, decrease nitrogen oxides, sulfur oxides, ammonia, and volatile organic compounds that are causative substances that generate fine dust (PM2.5) according to the light emission of the lamp 120, thereby purifying air in an interior in which a lighting device according to the present disclosure is installed.

Meanwhile, the ethanol contained in the above-described coating solution functions to improve adhesion of the NNT and the alkoxide, which are photocatalytic materials, to the surface of the lamp 120 made of polycarbonate during the coating process.

In detail, a manufacturer evenly applies the coating solution having the above-described component according to another embodiment of the present disclosure to the surface of the lamp 120 made of polycarbonate, and then heat-treats the surface of the lamp 120 at a predetermined heating temperature (for example, about 100° C. to 150° C.) for a predetermined time (for example, about 3 to 4 hours), thereby performing a coating treatment operation of the photocatalytic material on the surface of the lamp 120.

Meanwhile, the input part 140 is installed on an upper portion of the lamp 120, and a user inputs various operation commands for the air sterilization lamp device through the input part 140.

Figure 4:
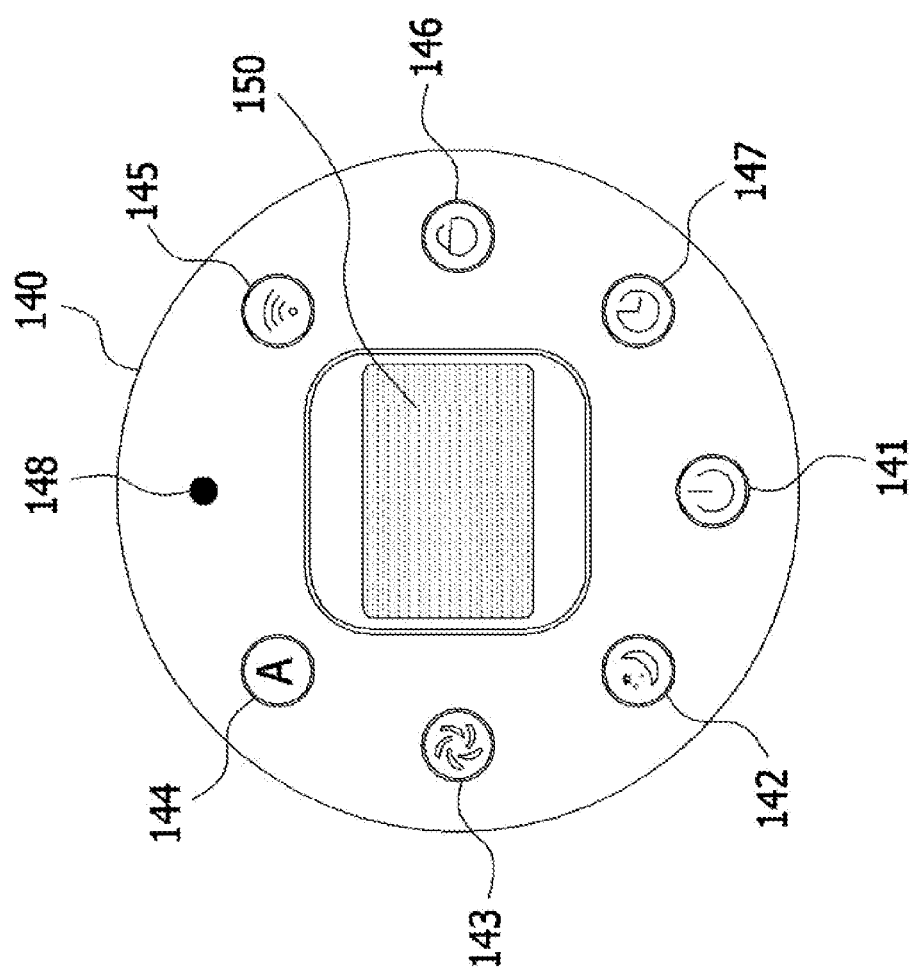
FIG. 4 is a view illustrating structures of an input part and a display part of the air sterilization lamp device according to the embodiment of the present disclosure.

FIG. 4 is a view illustrating structures of an input part and a display part of the air sterilization lamp device according to the embodiment of the present disclosure. As illustrated in FIG. 4, the input part 140 includes a plurality of input buttons through which the operation commands of the user for the air sterilization lamp device are input.

In detail, as illustrated in FIG. 4, it is preferable that the input part 140 includes a power button 141, a sleeping mode button 142, an intake fan operation button 143, an automatic operation button 144, a Wi-Fi module activation button 145, a lock button 146, and a timer button 147 for the air sterilization lamp device.

Meanwhile, the display part 150, which is a display device for displaying an operation state of the air sterilization lamp device, may be installed in the center of the input part 140 as illustrated in FIG. 4, and the display part 150 may additionally display a measurement value of the concentration of fine duct and a measurement value of the concentration of an organic compound, which are measured through a sensor provided in the body 110.

In addition, the input part 140 is installed on the upper portion of the lamp 120, and thus functions as an upper cover of the lamp 120 having a cylindrical structure. Meanwhile, an exhaust hole 148 is formed in the input part 140, and thus the outside air subjected to fine dust removal and sterilization treatment as described above while passing through the inside of the lamp 120 is supplied back to the outside through the exhaust hole 148.

In addition, it is preferable that in the implementation of the present disclosure, the filter 160 is also heat-treated in the same manner as the lamp 120 after being coated with the coating solution, which is a solution containing the photocatalytic material as described above.

According to the present disclosure, an air sterilization lamp device that can purify indoor air through a function of removing generated fine dust and performing sterilization treatment as a lamp coated with a coating solution containing a photocatalytic material is irradiated with light and, at the same time, can function as a lighting device is provided.

Terms used in the present disclosure are used only to describe specific embodiments and are not intended to limit the present disclosure. Singular expressions include plural expressions unless clearly otherwise indicated in the context. It should be understood in the present application that terms such as "include" or "have" are intended to indicate that there are features, numbers, steps, operations, components, parts, or combinations thereof that are described in the specification, and do not exclude in advance the possibility of the presence or addition of one or more other features, numbers, steps, operations, components, parts, or combinations thereof.

Although the exemplary embodiments and application examples of the present disclosure have been illustrated and described above, the present disclosure is not limited to the above-described specific embodiments and application examples. It is obvious to those skilled in the art to which the present disclosure belongs that various modifications can be made without departing from the spirit of the present disclosure. These modifications should not be individually understood from the technical spirit or perspective of the present disclosure.

What is claimed is:

1. An air sterilization lamp device comprising:
   a body having an intake hole and an intake fan provided therein and configured to take in outside air through the intake hole provided on an outer surface thereof;
   a lamp connected to and installed on the body, the lamp through which the outside air taken in by the body is introduced, a surface of the lamp coated with a photocatalytic material comprising titanium dioxide ($TiO_2$) doped with nitrogen (N) and nickel (Ni), the photocatalytic material produced by injecting nickel(II) chloride hexahydrate ($NiCl_2 \cdot 6H_2O$) and ammonium carbonate ($(NH_4)_2CO_3$) into a titanium dioxide ($TiO_2$) sol and stirring $NiCl_2 \cdot 6H_2O$ and $(NH_4)_2CO_3$ injected into the titanium dioxide ($TiO_2$) sol, the titanium dioxide ($TiO_2$) sol produced by reacting a mixed solution of a titanium tetra isopropoxide solution, diethanolamine, and 2-propanol while stirring the mixed solution at room temperature;
   a light emitting source installed inside the lamp and emitting light by power supplied from the body; and
   a filter installed at a connection portion between the body and the lamp.

2. The air sterilization lamp device of claim 1, wherein the filter is coated with a photocatalytic material.

3. The air sterilization lamp device of claim 1, wherein the surface of the lamp is heat-treated at heating temperature of 100° C. to 150° C. after the photocatalytic material has been applied to the surface of the lamp.

4. The air sterilization lamp device of claim 1, further comprising:
   an upper housing to which one end of the light emitting source is fixed, the upper housing having an input part and a display part;
   a lower housing to which the other end of the light emitting source is fixed; and
   the filter installed in the lower housing.

5. The air sterilization lamp device according to claim 1, wherein the body includes a sensor for measuring a concentration of fine dust and a concentration of a volatile organic compound, and the air sterilization lamp device is configured to remove the fine dust and the volatile organic compounds inside the lamp by the light irradiated from said lamp portion.

6. The air sterilization lamp device of claim 1, wherein a surface of the lamp is formed of a polycarbonate material coated with the photocatalytic material.

7. The air sterilization lamp device of claim 1, wherein the lamp is irradiated with light having a wavelength in the range of 580 nm to 640 nm from the surface of the lamp.

* * * * *